United States Patent
Yu

(10) Patent No.: US 9,132,004 B2
(45) Date of Patent: Sep. 15, 2015

(54) SILICON BREAST IMPLANT WHICH MINIMIZES STRESS CONCENTRATION AND METHOD FOR MANUFACTURING SAME

(76) Inventor: Won Seok Yu, Daejeon (KR)

(*) Notice: Subject to any disclaimer, the term of this patent is extended or adjusted under 35 U.S.C. 154(b) by 0 days.

(21) Appl. No.: 14/116,417

(22) PCT Filed: May 8, 2012

(86) PCT No.: PCT/KR2012/003582
§ 371 (c)(1),
(2), (4) Date: Dec. 11, 2013

(87) PCT Pub. No.: WO2012/176982
PCT Pub. Date: Dec. 27, 2012

(65) Prior Publication Data
US 2014/0107779 A1    Apr. 17, 2014

(30) Foreign Application Priority Data
Jun. 23, 2011    (KR) .................. 10-2011-0061273

(51) Int. Cl.
*A61F 2/12*    (2006.01)
*B29C 41/14*    (2006.01)
(Continued)

(52) U.S. Cl.
CPC . *A61F 2/12* (2013.01); *A61L 27/18* (2013.01); *B29C 41/14* (2013.01); *B29C 66/1282* (2013.01); *B29C 66/1286* (2013.01); *B29C 66/1288* (2013.01); *B29C 66/12822* (2013.01);
(Continued)

(58) Field of Classification Search
CPC .................. A61F 2/12; A61B 19/24
USPC ........................................... 623/8
See application file for complete search history.

(56) References Cited

U.S. PATENT DOCUMENTS 1,422,495 A * 7/1922 Thiele ................... 152/367
5,026,394 A * 6/1991 Baker ....................... 623/8
(Continued)

FOREIGN PATENT DOCUMENTS

EP          0872221 A1   10/1998
JP     2010-534551 A    11/2010
(Continued)

OTHER PUBLICATIONS

International Search Report (PCT/KR2012003582), WIPO, Nov. 23, 2012.

*Primary Examiner* — Thomas J Sweet
*Assistant Examiner* — Daniel Bissing
(74) *Attorney, Agent, or Firm* — Park & Associates IP Law, P.C.

(57) ABSTRACT

The present invention relates to a silicon breast implant which minimizes stress concentration applied thereto after being inserted into the human body to maximize the resistance of same to fatigue-induced rupture, thereby improving the durability of the implant. The breast implant may include an elegant patch-adhesion portion having a thin thickness so as to provide superior overall feel and improve the appearance of the product. Further, the breast implant has a silicon shell defining an outer wall thereof and the patch adhesion portion for closing, from the outside, a hole formed in a bottom surface of the silicon shell so that the patch adhesion portion is increased in strength to maximize adhesion durability, safety of use, and effectiveness. The silicon shell has a uniform overall thickness, and the patch adhesion portion comprises a patch hole through which a patch adheres to a lower end of the silicon shell using an adhesive material.

25 Claims, 8 Drawing Sheets

(51) Int. Cl.
  *B29C 65/00* (2006.01)
  *A61L 27/18* (2006.01)
  *B29L 31/00* (2006.01)
  *B29C 65/48* (2006.01)
  *B29C 65/02* (2006.01)

(52) U.S. Cl.
  CPC ........... *B29C 66/12842* (2013.01); *B29C 66/14* (2013.01); *B29C 66/30325* (2013.01); *B29C 66/5346* (2013.01); *B29C 66/71* (2013.01); *B29C 66/723* (2013.01); *A61L 2430/04* (2013.01); *B29C 65/02* (2013.01); *B29C 65/48* (2013.01); *B29C 66/1122* (2013.01); *B29C 66/1222* (2013.01); *B29C 66/1226* (2013.01); *B29C 66/1284* (2013.01); *B29L 2031/7532* (2013.01)

(56) References Cited

U.S. PATENT DOCUMENTS

| | | |
|---|---|---|
| 6,074,421 A | 6/2000 | Murphy |
| 2007/0093911 A1 | 4/2007 | Fricke et al. |
| 2009/0030515 A1* | 1/2009 | Schuessler et al. ............... 623/8 |
| 2009/0270985 A1* | 10/2009 | Schuessler ........................ 623/8 |
| 2011/0257743 A1 | 10/2011 | Schuessler |

FOREIGN PATENT DOCUMENTS

| | | |
|---|---|---|
| KR | 10-2010-0111190 A | 10/2010 |
| KR | 10-2011-0041990 A | 4/2011 |
| WO | 2010/056610 A2 | 5/2010 |

* cited by examiner (a)

(b)

(a)

(b)

( a )

( b )

(a)

(b)

(a)

(b)

(a)

(b)

SILICON BREAST IMPLANT WHICH MINIMIZES STRESS CONCENTRATION AND METHOD FOR MANUFACTURING SAME

REFERENCE TO RELATED APPLICATIONS

This application is a U.S. National Phase application of International Application No. PCT/KR2012/003582, filed May 8, 2012, and claims priority to Korean Patent Application No. 10-2011-0061273, filed Jun. 23, 2011, the disclosures of each of these applications being incorporated herein by reference in their entireties.

FIELD OF THE INVENTION

The present invention relates to an artificial breast prosthesis with minimized stress concentration and a method of manufacturing the same, and more particularly to an artificial breast prosthesis with minimized stress concentration and a method of manufacturing the same in which a silicone shell has a uniform thickness, a patch adhesion portion has the same thickness and physical properties as those of the silicone shell and is provided with a step portion and an uneven groove so that a patch is closely adhered to an inner surface of the silicone shell, and thus, after the artificial breast prosthesis is inserted into the human body, concentration of stress applied thereto is minimized and thus resistance to fatigue rupture is maximized whereby overall durability of the artificial breast prosthesis is enhanced, the patch adhesion portion has high adhesion strength against pressure applied to the prosthesis and thus has maximized adhesion durability, and the patch adhesion portion has a small thickness and a beautiful exterior appearance and thus the prosthesis has excellent overall feel and has increased appearance beauty whereby safety and efficacy of the artificial breast prosthesis may be maximized.

BACKGROUND OF THE INVENTION

In general, artificial breast prostheses are used in reconstructive plastic surgery for a breast when breast loss occurs due to diseases or accidents and in cosmetic surgery for a malformed breast. In terms of anatomy, artificial breast prostheses are also used for the substitution of organs or tissues.

Artificial breast prostheses are products in which a filling material, such as saline, hydro-gel, and silicone gel, is filled in an envelope formed of silicone that is implantable to an organ (hereinafter referred to as a "shell"). These artificial breast prostheses may be classified into round type products and water drop shaped products (anatomical type) according to the shape of a product, and may be classified into smooth products and textured products according to the surface conditions of a product. More particularly, the artificial breast prostheses will be described in brief as follows.

A saline filled artificial breast prosthesis is configured such that saline is injected or is injectable into a shell formed of silicone (more particularly, the shell being formed of polyorganosiloxane). The saline filled artificial breast prosthesis has a structure consisting of a silicone shell and a valve.

Although the saline filled artificial breast prosthesis ensures safety even if the filling material leaks into the human body after rupture of the shell as a result of using sterile saline as the filling material, and is easy to change the volume of a breast by adjusting the injection amount of saline, the saline filled artificial breast prosthesis is significantly deteriorated to the touch after surgery as compared to other artificial breast prostheses and the shell thereof has inferior durability.

A hydro-gel filled artificial breast prosthesis is configured such that hydro-gel composed of monosaccharide and polysaccharides is filled within the shell as in the above-described saline filled artificial breast prosthesis. The hydro-gel filled artificial breast prosthesis was developed based on the principle that the filling material can be absorbed into and excreted from the human body even if the filling material leaks due to rupture of the prosthesis.

A hydro-gel filled artificial breast prosthesis is configured such that hydro-gel composed of monosaccharide and polysaccharides is filled within the shell as in the above-described saline filled artificial breast prosthesis. The hydro-gel filled artificial breast prosthesis was developed based on the principle that the filling material can be absorbed into and excreted from the human body even if the filling material leaks due to rupture of the prosthesis.

However, in the case of the hydro-gel filled artificial breast prosthesis, long-term safety has not been established, volume change over time and occurrence of wrinkles may increase after the artificial breast prosthesis is implanted, and feeling is unnatural as compared to a silicone artificial breast prosthesis. Accordingly, the hydro-gel filled artificial breast prosthesis has not been distributed in the market since 2000 as safety thereof has yet to be proven.

A silicone gel filled artificial breast prosthesis is configured such that a shell is filled with a silicone gel having an appropriate viscosity. The silicone gel filled artificial breast prosthesis has superior product durability and a more pleasant texture than the saline filled artificial breast prosthesis and thus achieves a dominant position in the market. Although the Food and Drug Administration of the United States of America (FDA) has imposed limitations on use of silicone gel filled artificial breast prostheses due to safety issues, the use of silicone gel filled artificial breast prostheses was again allowed officially in 2006.

The silicone gel filled artificial breast prosthesis has been developed in the order of a first generation prosthesis, a second generation prosthesis, and a third generation prosthesis. This development history will be described in detail as follows.

The first generation silicone gel filled artificial breast prosthesis is a product sold from the middle of the 1960s to the middle of the 1970s, and was initially developed in 1961 by Cronin and Gerow. The first generation silicone gel filled artificial breast prosthesis can be represented in brief by the use of a thick shell, a smooth surface, and a high viscosity silicone gel. This prosthesis suffers from gel bleed and capsular contracture, but a rupture speed thereof is relatively low due to the use of the thick shell.

The second generation silicone gel filled artificial breast prosthesis is a product sold from the middle of the 1970s to the middle of the 1980s, and includes a thin shell and a silicone gel filling material of a low viscosity, for the sake of smoother texture. This prosthesis is characterized by a similar gel bleed rate, higher rupture occurrence, and lower capsular contracture as compared to the first generation prosthesis.

The third generation silicone gel filled artificial breast prosthesis is a product sold from the middle of the 1980s to the present, and includes a gel bleed barrier layer to prevent gel bleed. The third generation silicone gel filled artificial breast prosthesis includes a thicker shell and silicone gel of a higher viscosity as compared to the second generation prosthesis. In addition, a product having a rough surface has been developed, in order to reduce capsular contracture.

Such artificial breast prostheses commonly include a shell, a filling material, and a bonding portion (hereinafter referred to as a "patch bonding portion," which is a common term in the art to describe a portion in which a hole generated during a process of detaching a shell from a mold is closed).

Shells are mostly manufactured via dipping and thus have limited durability (particularly, fatigue rupture is a risk). Basically, the shell produced via dipping has a thickness difference in upper and lower portions of the shell due to gravity, and this thickness difference causes a portion of the shell to be relatively weak to stress.

To increase shell durability in consideration of fatigue rupture, absolute strength of a shell can be increased to some extent by increasing an overall thickness of the shell. This also has limitations in that a lower end of the shell is very thick while increasing the overall thickness of the shell and thus flexibility of the breast prosthesis is deteriorated. For example, in the case of a shell having an average thickness of 1 mm or less, the thickness of a lower end portion thereof increases by about 1 mm as the thickness of an upper end portion thereof increases by 0.3 mm, which results in a greater thickness difference.

In addition, processing of a patch bonding portion is performed using a patch (a patch bonding material) and an adhesive material. In conventional fabrication of artificial breast prostheses, a patch used as a bonding material in the patch bonding portion has the same thickness and physical properties as those of the shell.

In this regard, to prevent deterioration of patch strength, the patch has to have a multilayer sheet structure including a leakage prevention layer formed of low molecular weight silicone inside the patch. However, it is very difficult to industrially and technically fabricate a patch in the form of a thin film including the leakage prevention layer therein and having a smaller thickness than the shell. Thus, a portion taken by cutting a shell is commonly used as the patch in the art.

That is, as illustrated in FIG. 1(a), a conventional breast prosthesis uses a patch 6 having the same thickness as that of the thickness (an average thickness of 0.5 to 1 mm) of a silicone shell (portions 5 and 7) and thus the thickness of patch bonding portions 8a and 8b, in which portions of the patch 6 and the silicone shell overlap each other, significantly increases and elongation characteristics of the patch bonding portions are very poor. In addition, in the case of a conventional breast prosthesis illustrated in FIG. 1(b), a central portion of a patch bonding portion is thinner than peripheral portions thereof and thus stress concentration occurs due to differences in physical properties at a boundary portion between the portion 7 of the silicon shell and each of the patch bonding portions 8a and 8b and, accordingly, problems in terms of resistance to fatigue of the patch 6 occur. Due to this, clinical studies have shown that rupture around a patch of an artificial breast prosthesis very frequently occurs.

U.S. Pat. No. 6,074,421 as the related art for such patch bonding portions discloses a patch bonding portion of a seamless artificial breast prosthesis. The present application relates to patch bonding technology for a patch bonding portion having the structure illustrated in FIG. 1(b) and discloses an artificial breast prosthesis in which a shell 7 has inclined edges at a hole thereof in an adhesion region between the patch 6 and the shell 7 and thus there is no seam-line formed between the patch 6 and the shell 7, whereby the artificial breast prosthesis has beautiful exterior appearance.

However, the above-described related art focuses only on improvement in terms of exterior appearance of the artificial breast prosthesis and does not consider improvement in overall performance, including durability, of the artificial breast prosthesis. Thus, the artificial breast prosthesis has a beautiful overall exterior appearance, while it uses a patch having the same thickness as that of the shell and thus the patch bonding portion is partially very thick and a central portion thereof is thin and, accordingly, there are differences in elongation and tension properties between each of the patch bonding portions and the silicone shell and stress concentration occurs due to differences in physical properties at a boundary portion between the shell and each of the patch bonding portions, resulting in deteriorated resistance to fatigue, which is the same problem as that of other existing artificial breast prosthesis fabrication technologies.

In addition, EP 0872221A1 as another related art similar to the above-described related art discloses patch bonding portions of a seamless artificial breast prosthesis and basically discloses the technical feature illustrated in FIG. 1(b) and further discloses an artificial breast prosthesis patch bonding technology characterized by a feature illustrated in FIG. 2(a). The present related art discloses an artificial breast prosthesis manufactured by forming a layer as illustrated in FIG. 2 at an outer side of a shell 7 in the vicinity of a hole to be closed by a patch 6 and bonding the patch 6 thereto and thus there are no seam-lines at bonding portions of the shell 7 and the patch 6, whereby the artificial breast prosthesis has a beautiful exterior appearance.

In this regard, although the patch bonding portions as illustrated in FIG. 1, i.e., overlapping portions 8a and 8b between the shell 7 and the patch 6, are not formed at an outside of the shell 7, as illustrated in FIG. 2(a), a central portion of the patch 6 has a smaller thickness than that of the patch bonding portions as in the aforementioned related art and thus stress concentration occurs at boundary portions of the patch bonding portions due to difference in physical properties between each patch bonding portion and the silicone shell, resulting in deteriorated resistance to fatigue, which is the same problem as that of other existing artificial breast prosthesis fabrication technologies.

In addition, as illustrated in FIG. 2(a), there is a hole with a tilted cross-section formed at an outer side of the shell 7 and bonding between the shell 7 and the patch 6 is not satisfactorily formed due to the hole and thus, in fact, seam-lines between the shell 7 and the patch 6 are formed, which makes it difficult for the present related art to achieve technical goals thereof.

In addition, as illustrated in FIG. 2(b), directions of pressure applied to a patch adhesion portion disposed at a rear surface of an artificial breast prosthesis in accordance with main pressure applied to the artificial breast prosthesis by motion or movement of a user after insertion into the human body are represented by arrows illustrated in FIGS. 2(a) and 2(b).

The above-described adhesion structure has a structure in which a hole of a shell is closed from the outside and, as illustrated in FIG. 2, when compared to an artificial breast prosthesis, a hole of which is closed from inside, in terms of pressure applied to the prosthesis, the patch adhesion structure is easily detached mechanically. In addition, in the above-described adhesion structure, pressure applied to the artificial breast prosthesis according to movement of a user after surgical implantation is concentrated in a narrower area than pressure applied to the patch adhesion portion, and thus, the adhesion structure has poor durability when compared to a patch adhesion structure that disperses pressure over a wider area, such as a structure in which a hole of a shell is closed from the inside. Thus, it is obvious that a structure in which a layer or a step is disposed at the inside of the shell and a patch is adhered thereto has mechanical and physical resistance to pressure applied to the artificial breast prosthesis after surgical implantation and excellent adhesion durability.

However, it is very difficult to adhere a patch to a shell provided thereat with a layer or a step with no gap therebetween from technical and industrial perspectives. This is because technology for forming a layer or a step at the inside of the shell and adhering a patch to the shell with no gap therebetween is incomparably difficult in terms of degree of difficulty, when compared to the above-described technology for forming a layer or a step at the outside of a shell and adhering a patch to the shell with no gap therebetween.

In addition, the aforementioned related arts are limited only in terms of exterior appearance improvement of products, not considering technical solutions in terms of physical characteristics and durability of a product and each element thereof. Thus, the above-described related arts do not technically consider pressure applied to the adhesion structures according to movement of a user after surgical implantation, adhesion durability against pressure, and overall durability of the artificial breast prostheses.

In addition, conventionally, as in the enlarged region illustrated in FIG. 2(a), a gap or crack 12 is generated at an adhesion boundary point 13 of the adhesion portion between the shell 7 and the patch 6.

This is because, in the related art or currently-used technologies, liquid silicone rubber (LSR) or silicone gum with little fluidity and having a very high viscosity has to be used as a bonding material 11 used in a process of adhering an already-hardened silicone shell to an already-hardened patch with a certain thickness. In other words, in a process of completely adhering the patch to a layer or step with angled edges formed at the silicone shell, a bonding material or adhesive 11, such as LSR or silicone gum having high viscosity, is not coated on side surfaces of the patch and only a lower end portion thereof is coated such that side surfaces of the shell and the patch are not adhered to each other.

It is obvious that such gap or crack deteriorates durability of an artificial breast prosthesis which is subjected to substantial stress and fatigue over time after surgical implantation.

The adhesion structures of the aforementioned related arts focus only on exterior appearance improvement of artificial breast prostheses and do not consider improvement in physical properties including adhesion durability and overall durability of the prostheses.

In addition, a filling material is injected into the inner space of a shell using a needle of a separate syringe device, and the needle is removed after injection of the filling material is completed. In this regard, a fine hole (hereinafter referred to as an "inlet") is formed after removal of the needle. Conventionally, as illustrated in FIG. 3(a), leakage of a filling material is prevented by sealing a lower portion of a patch 6 at which an inlet 3 is formed using silicone 4 for sealing, such as a silicone solution, silicone gum, or the like so as to prevent the filling material from leaking via the inlet 3 formed after injection of the filling material, or, as illustrated in FIG. 3(b), first, a frame 2 having a ring shape is prepared, a central portion thereof is perforated using a needle so as to allow the filling material to be injected therethrough, the inlet 3 is sealed by silicone 4 for sealing, such as a silicone solution, silicone gum, or the like after injection of the filling material to prevent the filling material injected into the shell from leaking to the outside.

However, when a conventional structure and fabrication method for sealing the inlet 3 is used, the silicone 4 for sealing applied to seal the inlet 3 and edges thereof are exposed to the outside and thus provide poor exterior appearance, and the silicone 4 and the edges thereof rub against the outside and thus may be easily detached.

Such phenomenon frequently occurs when a filling material used for injection sticks in a region to be coated with the silicone 4 or to which the silicone 4 is to be applied. Such phenomenon almost inevitably occurs in filling and hardening processes in manufacture of an artificial breast prosthesis, which is addressed using a method of sealing the inlet 3 after wiping leaked filling material off of the inlet 3. However, the inlet 3 is sealed with the filling material leaked due to operator carelessness such as incomplete wiping and thus the silicone 4 for sealing the inlet 3 may be easily detached.

As such, the filling material injected into the shell may leak to the outside and, accordingly, product quality and safety is significantly reduced.

To address these problems, Korean Patent Application Publication No. 10-2011-0041990 discloses prevention of leakage of a filling material by, as illustrated in FIG. 4(a), forming a filling material injection groove 9 having a concave shape, which is a space through which the filling material is injected into an inner space of a silicone shell using a needle, at a central portion of a lower surface of a patch part 6 and then sealing the filling material injection groove 9 using silicone 9a, such as a silicone solution, silicone gum, or the like after injection of the filling material. Due to such configuration, the silicone 9a used to seal an inlet and edges thereof are not exposed to the outside, whereby detachment of the silicone 9a due to external rubbing may be prevented as much as possible.

However, as described above, problems in terms of weak adhesive strength of an inlet sealing portion due to leakage of a filling material remain to be solved.

SUMMARY OF THE INVENTION

Therefore, the present invention has been made in view of the above problems, and it is an object of the present invention to provide a silicone artificial breast prosthesis with minimized stress concentration and a method of manufacturing the same in which a silicone shell has a uniform thickness and a patch adhesion portion has the same thickness as that of the silicone shell and the same or similar physical properties (expansibility, strength, elasticity, and the like) as the silicone shell, and thus, stress concentration occurring due to differences in physical properties between the silicone shell and the patch adhesion portion is minimized and resistance to fatigue rupture is maximized and, accordingly, rupture of the silicone artificial breast prosthesis, which is the most dangerous complication, is significantly reduced, whereby safety and efficacy of the artificial breast prosthesis may be enhanced.

It is another object of the present invention to provide a silicone artificial breast prosthesis with minimized stress concentration and a method of manufacturing the same in which the patch adhesion portion, which is disposed at an inner side of the silicone shell, includes a step portion and an uneven groove and has an adhesion structure having high mechanical and physical resistance to pressure applied to the silicone artificial breast prosthesis in which a patch is adhered to an inner surface of the silicone shell, and the patch adhesion portion adhered to the silicone shell has increased adhesion area and adhesive strength and thus has excellent adhesion durability.

It is another object of the present invention to provide a silicone artificial breast prosthesis with minimized stress concentration and a method of manufacturing the same in which neither a gap nor a crack is formed at an adhesive boundary point between the silicone shell and a silicone shell and a patch and thus a patch adhesion portion has excellent adhesion durability.

It is another object of the present invention to provide a silicone artificial breast prosthesis with minimized stress concentration and a method of manufacturing the same in which a silicone shell including a patch adhesion portion has a uniform overall thickness and thus the silicone artificial breast prosthesis has superior overall feel, whereby product efficacy and quality are increased.

It is further object of the present invention to provide a silicone artificial breast prosthesis with minimized stress concentration and a method of manufacturing the same in which an inlet is formed through injection of a filling material and silicone is used as a sealant to close the inlet and a sealing process is doubly performed so as to prevent exposure of edges of the sealant to the outside, and thus, an inlet sealing portion has beautiful exterior appearance and enhanced quality, and the inlet sealing portion has enhanced adhesive strength and high resistance to fatigue rupture and thus there is no risk of detachment of the sealant from the inlet sealing portion, whereby safety and efficacy of the silicone artificial breast prosthesis may be maximized.

In accordance with an aspect of the present invention, the above and other objects can be accomplished by the provision of a silicone artificial breast prosthesis with minimized stress concentration including a silicone shell forming an outer wall thereof and a patch adhesion portion for closing a hole formed in a lower surface of the silicone shell from the outside, wherein the silicone shell has a uniform overall thickness, the patch adhesion portion has a patch hole through which a patch is adhered as an adhesive to an inner lower end of the silicone shell, and the patch adhesion portion in which the patch is adhered to the patch hole has the same thickness as that of the silicone shell and the same or similar physical properties as the silicone shell.

The patch hole may have at least one step portion having a step and formed at an inner surface of a portion of the silicone shell contacting the patch.

The patch hole may have a slope such that the patch hole increases in diameter towards the step portion from a bottom of the patch hole to an upper side thereof. The patch hole may be configured such that a diameter of the patch hole on an inner side of the silicone shell is greater than that of the patch hole on an outer side of the silicone shell.

The patch hole may have a slope such that the patch hole increases in diameter towards the step portion from a bottom of the patch hole to an upper side thereof.

The patch hole may have a rounded concave curved surface formed along an outer circumference of the step portion.

The patch adhesion portion may have at least one uneven groove at a surface of the patch adhesion portion contacting the patch so that an adhesion area between the patch adhesion portion and the patch increases and adhesion durability therebetween is enhanced so as to prevent the patch from detaching from the patch adhesion portion.

The uneven groove may have a V-letter shape, the uneven groove may have a U-letter shape, and the uneven groove may have a shape.

The patch may include a leakage prevention layer of low molecular weight silicone and at least one thin film patch formed thin.

The patch adhesion portion may include a bonding material or an adhesive disposed between the silicone shell and the patch so as to enable smooth adhesion therebetween.

The patch adhesion portion may be completely adhered such that an inner surface of the silicone shell and an inner surface of the patch form the same horizontal plane to prevent occurrence of a gap or a crack at an adhesion boundary point between the silicone shell and the patch.

The patch adhesion portion may include an inlet formed above a lower surface thereof so that a filling material is injected into an inner space of the silicone shell and a filling material injection groove disposed below the inlet, having a multilayered structure comprising at least two layers to a small depth, and concavely formed.

The filling material injection groove may include a first sealing portion formed by primarily sealing a space at a lower side of the inlet so as to close the inner space of the silicone shell from the outside and a second sealing portion formed by secondarily sealing a space at a lower side of the first sealing portion to be finishing-processed so as to prevent the filling material injected into the inner space of the silicone shell from leaking to the outside.

When stress is applied to the adhesion boundary point at which the silicone shell and the patch are adhered to each other, the stress may be dispersed in at least two axial directions such that stress applied in accordance with left and right tensile forces and stress applied according to tensile force in an inclination angle direction of a cross-section of the step portion or uneven groove and in an inclination angle direction of a cut cross-section of the patch hole are simultaneously applied to the patch adhesion portion.

In accordance with another aspect of the present invention, a method of manufacturing a silicone artificial breast prosthesis includes a silicone solution dipping step of dipping a breast shaped mold into a silicone solution to obtain a silicone shell, a drying and hardening step of drying and hardening the silicone shell attached to the mold using a drier to obtain a silicone shell, an artificial breast shell obtaining step of perforating a hole in a lower end of the silicone shell attached to the mold and detaching and obtaining the silicone shell from the mold, a patch hole formation step of forming a patch hole comprising a step portion and an uneven groove so as to adhere a patch to an inner surface portion of the silicone shell, corresponding to a hole of the silicone shell, the patch hole being formed through which the patch is adhered to the hole of the silicone shell, a patch structure molding step of molding the patch comprising a thin film patch and an adhesive in accordance with shapes of a step of the step portion and the uneven groove in addition to a circumference and thickness corresponding to the patch hole so that the patch is completely adhered to the patch hole with no gap therebetween, a patch adhesion step of adhering the molded patch structure comprising the thin film patch and the adhesive to the patch hole of the silicone shell, a filling material injection groove processing step of forming a filling material injection groove having a concave, multilayered structure at a lower surface of the patch, through which a filling material is injected into the inner space of the silicone shell, a filling step of filling the inner space of the silicone shell through injection of the filling material through an inlet below which the filling material injection groove is formed, and a finishing step of forming a first sealing portion and a second sealing portion in this order by doubly sealing the filling material injection groove using a sealant so as to prevent the filling material filling the inner space of the silicone shell from leaking to the outside via the inlet, the inlet being a fine hole formed by a syringe needle when injecting the filling material.

According to a silicone artificial breast prosthesis with minimized stress concentration and a method of manufacturing the same, according to embodiments of the present invention, a silicone shell has a uniform thickness and a patch adhesion portion has the same thickness as that of the silicone shell and the same or similar physical properties (expansibility, strength, elasticity, and the like) to the silicone shell, and thus, stress concentration occurring due to differences in physical properties between the silicone shell and the patch adhesion portion is minimized and resistance to fatigue rupture is maximized and, accordingly, rupture of the artificial breast prosthesis, which is the most dangerous complication, is significantly reduced, whereby safety and efficacy of the artificial breast prosthesis may be maximized.

In addition, the patch adhesion portion includes a step portion and an uneven groove and has an adhesion structure having high mechanical and physical resistance to pressure applied to the artificial breast prosthesis in which a patch is adhered to an inner surface of the silicone shell. In this regard, the adhesion structure increases an adhesion area and allows stress to be dispersed in at least two axial directions, and thus, adhesive strength is mechanically and physically increased and adhesion durability of the patch adhesion portion is enhanced, which results in enhanced overall safety of the artificial breast prosthesis.

In addition, the patch adhesion portion has a structure in which neither a gap nor a crack is formed at an adhesion boundary point between the silicone shell and the patch and thus may have enhanced adhesion durability.

In addition, the silicone shell, including the patch and the patch adhesion portion, has a uniform overall thickness and thus the artificial breast prosthesis has excellent overall feel and, accordingly, may have high efficacy and quality.

In addition, a finishing process is performed through double sealing so that an inlet formed through injection of a filling material and a silicone sealant for closing the inlet or edge portions thereof are not exposed to the outside, and thus, beautiful appearance of the sealing portion of the inlet may be achieved.

Moreover, sealing portions of a filling material injection groove have an increased adhesion area due to a multilayered structure thereof and a sealable silicone used in sealing of the inlet and edge portions thereof do not rub against the outside, and thus, an inlet sealing portion has increased adhesive strength and enhanced resistance to fatigue rupture and, accordingly, there is no risk of detachment of the sealable silicone from the inlet sealing portion, which results in increased protection against leakage of the filling material.

Furthermore, the filling material injection groove has a multilayered structure and doubly seals the inlet, and thus, deterioration of adhesive strength of the sealing portion of the inlet due to leakage of the filling material via the inlet occurring in the filling process may be prevented and problems occurring due to operator error may also be addressed, and thus, protection against leakage of the filling material may be maximized.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
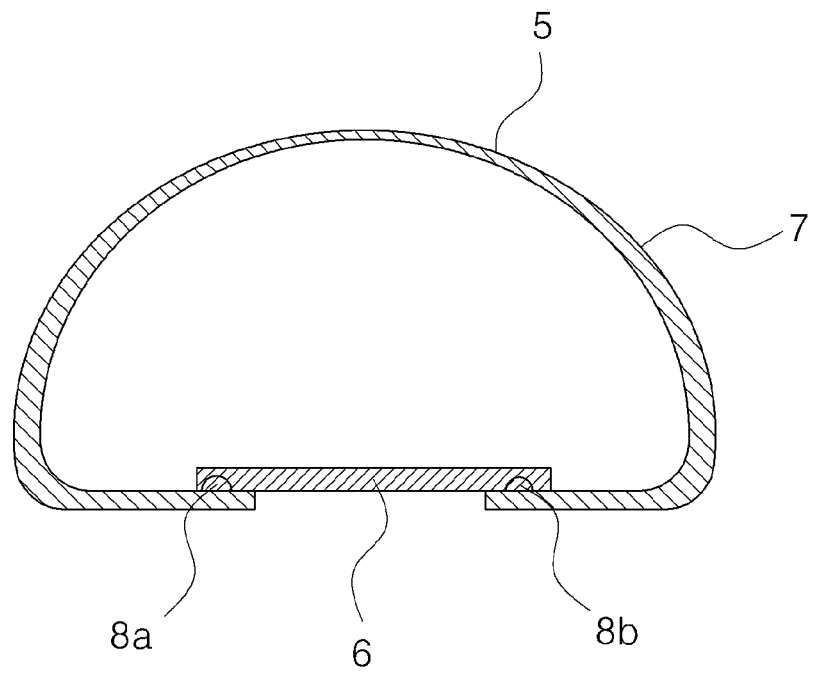
FIGS. 1(a) and 1(b) are views illustrating examples of a silicone shell and a patch adhesion portion of a conventional artificial breast prosthesis.
Figure 1:
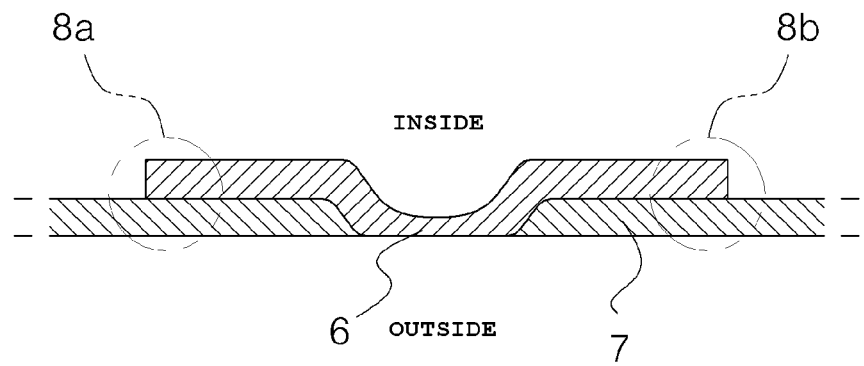

According to an embodiment of the present invention, there is provided a silicone artificial breast prosthesis with minimized stress concentration including a silicone shell forming an outer wall thereof and a patch adhesion portion for closing a hole formed in a lower surface of the silicone shell from the outside, in which the silicone shell has a uniform overall thickness, the patch adhesion portion has a patch hole through which a patch is adhered as an adhesive material to an inner lower end of the silicone shell, and the patch adhesion portion in which the patch is adhered to the patch hole has the same thickness as that of the silicone shell and the same or similar physical properties as the silicone shell.

In addition, the silicone artificial breast prosthesis with minimized stress concentration is characterized in that the patch hole has at least one step portion having a step and formed at an inner surface of a portion of the silicone shell contacting the patch.

In addition, the silicone artificial breast prosthesis with minimized stress concentration is characterized in that the patch hole is configured such that the diameter of the patch hole on the inner side of the silicone shell is greater than that of the patch hole on the outer side of the silicone shell.

In addition, the silicone artificial breast prosthesis with minimized stress concentration is characterized in that the patch hole has a slope such that the patch hole increases in diameter towards the step portion from the bottom of the patch hole to an upper side thereof.

In addition, the silicone artificial breast prosthesis with minimized stress concentration is characterized in that the patch hole has a rounded concave curved surface formed along an outer circumference of the step portion.

In addition, the silicone artificial breast prosthesis with minimized stress concentration is characterized in that the step portion of the patch hole has at least one uneven groove at a surface of the step portion contacting the patch so that an adhesion area between the step portion and the patch increases and adhesion durability therebetween is enhanced so as to prevent the patch from detaching from the patch adhesion portion.

In addition, the silicone artificial breast prosthesis with minimized stress concentration is characterized in that the patch adhesion portion includes at least one thin film patch completely adhered and formed thin so as to form the same horizontal plane as an inner lower surface of the silicone shell at an upper portion of the patch, to prevent occurrence of a gap or a crack at an adhesion boundary point between the silicone shell and the patch.

In addition, the silicone artificial breast prosthesis with minimized stress concentration is characterized in that the patch adhesion portion includes an inlet formed above a lower surface thereof so as to inject a filling material into an inner space of the silicone shell and a filling material injection groove disposed below the inlet, having a multilayered structure including at least two layers to a certain depth, and concavely formed.

In addition, the silicone artificial breast prosthesis with minimized stress concentration is characterized in that the filling material injection groove includes a first sealing portion for primarily sealing a space on a lower side of the inlet so as to close an inner space of the silicone shell from the outside and a second sealing portion for secondarily sealing a space on a lower side of the first sealing portion to be finishing-processed so as to prevent the filling material injected into the inner space of the silicone shell from leaking to the outside.

In addition, the silicone artificial breast prosthesis with minimized stress concentration is characterized in that, when stress is applied to an adhesion boundary point at which the silicone shell and the patch are adhered to each other, the stress is dispersed in at least two axial directions such that stress applied in accordance with left and right tensile forces and stress applied according to tensile force in an inclination angle direction of a cross-section of the step portion or uneven groove and in an inclination angle direction of a cut cross-section of the patch hole are simultaneously applied to the patch adhesion portion.

According to another embodiment of the present invention, there is provided a method of manufacturing the silicone artificial breast prosthesis including: a silicone solution dipping step of dipping a breast shaped mold into a silicone solution to obtain a silicone shell; a drying and hardening step of drying and hardening the silicone shell attached to the mold using a drier to obtain a silicone shell; an artificial breast shell obtaining step of perforating a hole in a lower end of the silicone shell attached to the mold and detaching the silicone shell from the mold; a patch hole formation step of forming a patch hole including a step portion and an uneven groove so as to adhere a patch to an inner surface portion of the silicone shell corresponding to a hole of the silicone shell; a patch structure molding step of molding the patch including a thin film patch and an adhesive material in accordance with the shapes of the step and the uneven groove in addition to a circumference and thickness corresponding to the patch hole so that the patch is completely adhered to the patch hole with no gap therebetween; a patch adhesion step of adhering the molded patch structure including the thin film patch and the adhesive material to the patch hole of the silicone shell; a filling material injection groove processing step of forming a filling material injection groove having a concave, multilayered structure at a lower surface of the patch, through which a filling material is injected into an inner space of the silicone shell; a filling step of filling an inner space of the silicone shell through injection of the filling material through an inlet below which the filling material injection groove is formed; and a finishing step of forming a first sealing portion and a second sealing portion in this order by doubly sealing the filling material injection groove using a sealant so as to prevent the filling material filling the inner space of the silicone shell from leaking to the outside from the inlet, which is a fine hole through which the filling material is injected using a syringe needle.

Hereinafter, a silicon artificial breast prosthesis with minimized stress concentration and a method of manufacturing the same, according to exemplary embodiments of the present invention, will be described in detail with reference to the accompanying drawings.

However, the present invention may be embodied in many different forms and should not be construed as being limited to embodiments set forth herein. Rather, these embodiments are provided so that this disclosure will fully convey the scope of the invention to those skilled in the art, and shapes of elements illustrated in the drawings are provided for illustrative purposes and clarity only.

First, according to an embodiment of the present invention, as illustrated in FIGS. 5 to 10, a silicon artificial breast prosthesis I includes a silicone shell 10 forming an outer wall thereof and a patch adhesion portion P for closing a hole formed in a lower surface of the silicone shell 10 from the outside, in which the patch adhesion portion P includes a patch 20 and a patch hole 11.

The silicone shell 10 having a uniform thickness is prepared by shaping the silicone shell 10 using a mold (not shown), forming, in a lower surface of the silicone shell 10, a hole through which the silicone shell 10 is taken out of the mold, and forming the patch hole 11 through which the patch 20 adheres to the silicone shell 10.

The silicone shell 10 has a uniform overall thickness.

The thickness of the silicone shell 10 may be variously adjusted, but may be between 0.5 and 2 mm in consideration of safety and efficiency.

The patch adhesion portion P is configured to close the inside of the silicone shell 10 from the outside and to close the patch hole 11 from the outside such that the inside of the silicone shell 10 remains filled with a filling material.

The patch hole 11 defines a frame of the patch adhesion portion P and is a portion to which the patch 20 adheres, and may be formed by adhering the patch 20 to a lower end portion of the silicone shell 10 using an adhesive.

Figure 5:
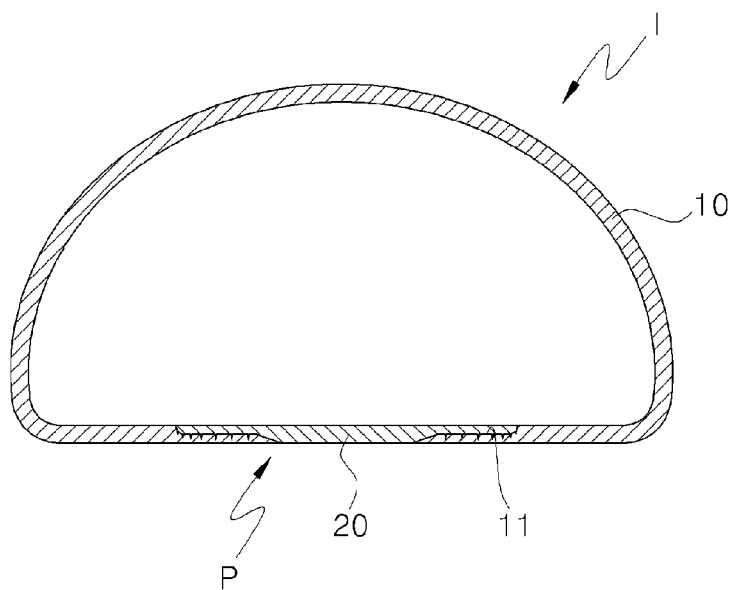
FIG. 5 is a sectional view of an artificial breast prosthesis according to an embodiment of the present invention.
Figure 6:
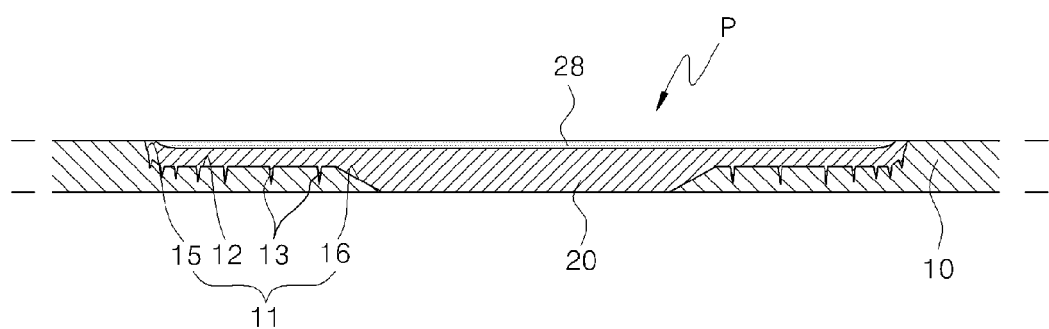
FIG. 6 is an enlarged sectional view of a patch adhesion portion, according to an embodiment of the present invention.

As illustrated in FIGS. 5 and 6, the patch hole 11 has at least one step portion 12 having a step and formed at an inner surface of a portion of the silicone shell 10 contacting the patch 20.

Due to formation of the step portion 12, the patch hole 11 is formed such that the diameter of an upper portion of the patch hole 11 is greater than that of a lower portion of the patch hole 11.

The height of the step portion 12 may be variously adjusted. The step portion 12 preferably has a height of 0.25 mm to 1.5 mm in consideration of the fact that the overall thickness of the silicone shell 10 is between 0.5 and 2 mm.

The patch hole 11 has a slope 16 inclined such that the patch hole 11 has a diameter that increases towards the step portion 12 from the bottom of the patch hole 11 to an upper side thereof. That is, as illustrated in FIG. 6, the slope 16 has an inclination angle of 45° or less with respect to a horizontal line of the lower surface of the silicone shell 10.

The patch hole 11 has a rounded concave curved surface 15 formed along an outer circumference of the step portion 12. That is, the curved surface 15 is formed at a position extending from an outer end of the step portion 12 to an inner surface of the silicone shell.

Figure 7:
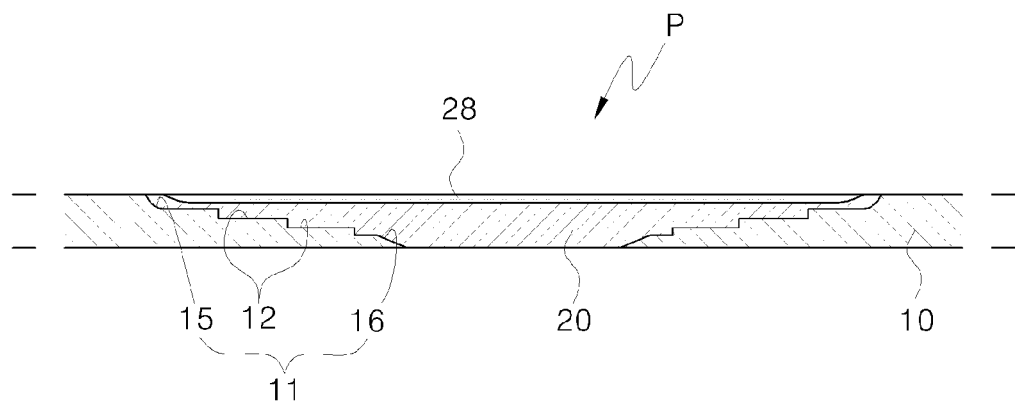
FIG. 7 is an enlarged sectional view of a patch adhesion portion, according to another embodiment of the present invention.
Figure 8:
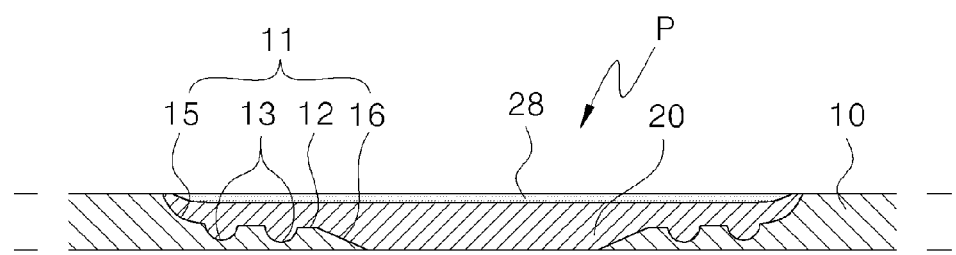
FIGS. 8(a) and 8(b) are enlarged sectional views illustrating an uneven groove of the patch adhesion portion, according to embodiments of the present invention.
Figure 8:
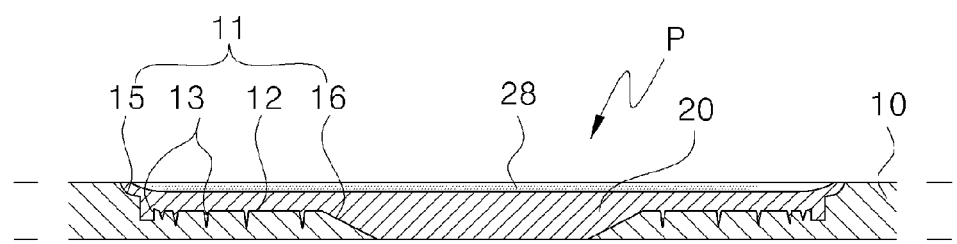

In addition, as illustrated in FIG. 7, the step portion 12 of the patch hole 11 may have a structure including a plurality of layers, i.e., a multilayered structure. In particular, the step portion 12 may have several steps that extend from an end of the slope 16 to an end of the curved surface 15, have a small size, and have a uniform height.

As illustrated in FIG. 6, uneven grooves 13 are formed to a fine depth at a surface of the step portion 12 of the patch hole 11, contacting the patch 20.

The uneven grooves 13 may be formed at a constant interval and the number thereof may be one or more. In particular, the grooves 13 may be formed at the step portion 12 to have an interval decreasing towards the curved surface 15 from the slope 16.

The uneven groove 13 may be in the form of a groove with a predetermined depth and have a downwardly sharp shape, i.e., a V-letter shape. In addition, as illustrated in FIG. 8(a), the uneven groove 13 may have a smoothly downwardly curved shape, i.e., a U-letter shape.

In addition, as illustrated in FIG. 8(b), the uneven groove 13 may be formed at the curved surface 15, which is an end portion of the step portion 12, to a shape so that the patch 20 can more closely adheres to the lower end portion of the silicone shell 10.

As described above, by forming the uneven groove 13 at the step portion 12 of the patch hole 11, an adhesion area between the silicone shell 10 and the patch 20 is increased and adhesion durability therebetween is improved, and thus, separation of the patch 20 from the patch adhesion portion P may be prevented.

The patch adhesion portion P in which the patch 20 is adhered to the patch hole 11 has the same thickness as that of the silicone shell 10 and has the same or similar physical properties as those of the silicone shell 10.

The patch 20 is adhered to the patch hole 11 to correspond to the thickness and size of the patch hole 11 and includes a leakage prevention layer (not shown) of low molecular weight silicone so as to prevent physical properties of the patch 20 from being deteriorated by a filling material (not shown).

The patch adhesion portion P, i.e., an adhesion structure between the silicone shell 10 and the patch 20, has no gap or crack at an adhesion boundary point therebetween.

The patch adhesion portion P includes a bonding material or an adhesive disposed between the silicone shell 10 and the patch 20 so as to enable smooth adhesion therebetween.

The patch adhesion portion P includes at least one thin film patch 28 completely adhered and formed thin so as to form the same horizontal plane as an inner lower surface of the silicone shell 10 at an upper portion of the patch 20, to prevent occurrence of a gap or a crack at the adhesion boundary point between the silicone shell 10 and the patch 20 and to form a patch adhesion portion P having strong mechanical and physical resistance to pressure applied to the silicone artificial breast prosthesis I.

The thin film patch 28 may have a fine thickness and the thickness thereof may be variously adjusted. Preferably, the thin film patch 28 has a thickness of 200 μm or less based on the fact that preferred thicknesses of the silicone shell 10 and the patch adhesion portion P are between 0.5 and 2 mm.

In the present invention, the overall configuration uses the following materials.

Basically, polyorganosiloxane, having silane as a main chain and an organo group, such as a methyl group, linked to the main chain, is used. The most representative example of the polyorganosiloxane is polydimethylsiloxane having a methyl group linked to a main chain. A methyl group of dimethylsiloxane, which is a monomer of polydimethylsiloxane, may be substituted with an organo group such as an alkyl group, a phenyl group, a vinyl group, or the like.

For example, a polymer obtained by polymerization of a monomer obtained by substituting dimethylsiloxane with methyl hydrogen siloxane, methyl phenyl siloxane, diphenyl siloxane, dimethyl vinyl siloxane, tri-fluoro propyl siloxane, or the like may be used. In addition, copolymers using oligomers consisting of these monomers may be used.

In particular, the thin film patch 28 uses silicone polymers that have molecular orientation, are highly dense, and have high binding affinity therebetween and thus are structurally stable, and a barrier film formed of a silicone elastomer through which low molecular weight silicone oil molecules (a filling material) have difficulty passing physically and chemically, is disposed as an intermediate layer between silicone polymer layers. In addition, the thickness of the barrier film may be variously adjusted in order to achieve blocking effects, but the barrier film may have a thickness of 10 to 80 μm in consideration of safety and efficiency.

For example, when the thin film patch 28 is formed of a polymer obtained through polymerization of diphenylpolysiloxane and dimethylpolysiloxane, the barrier film formed as the intermediate layer of the thin film patch 28 may be formed of a silicone elastomer obtained through polymerization of dimethylpolysiloxane and methyl 3,3,3-trifluoropropylpolysiloxane or diphenylpolysiloxane.

Figure 9:
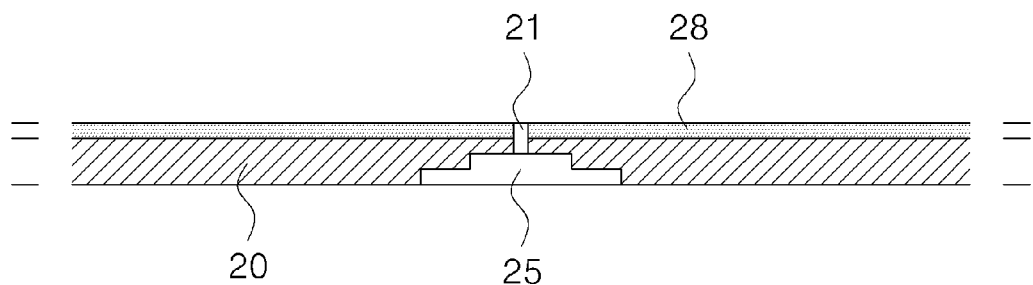
FIG. 9 is an enlarged sectional view illustrating a state in which a finishing step for sealing a filling material injection groove using a sealant according to a patch has yet been performed, according to an embodiment of the present invention.

As illustrated in FIG. 9, the patch adhesion portion P includes an inlet 21 formed above a lower surface thereof so that a filling material can be injected into an inner space of the silicone shell 10 and a filling material injection groove 25 disposed below the inlet 21, having a multilayered structure including at least two layers to a small depth, and concavely formed. More specifically, the filling material injection groove 25, formed at a lower surface of the patch 20 to a certain depth, having a multilayered structure, and concavely formed, is first formed, and then the inlet 21, having a structure connected to the inner space of the silicone shell 10 and thus being formed by injection when injecting the filling material using a separate syringe device, is formed above the filling material injection groove 25.

The depth of the filling material injection groove 25 may be variously adjusted, but the filling material injection groove 25 may have a depth of 0.3 to 1.5 mm in consideration of efficiency.

Figure 10:
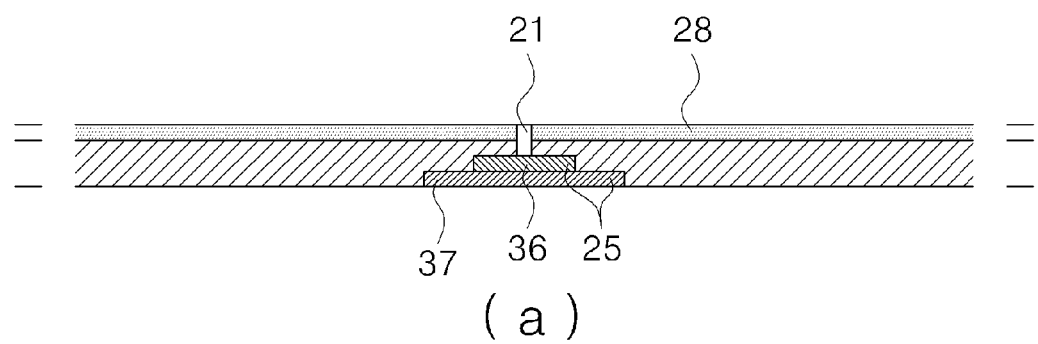
FIGS. 10(a) and 10(b) are enlarged sectional views illustrating states in which a finishing step for sealing a filling material injection groove using a sealant according to a patch has been completed, according to an embodiment of the present invention.
Figure 10:
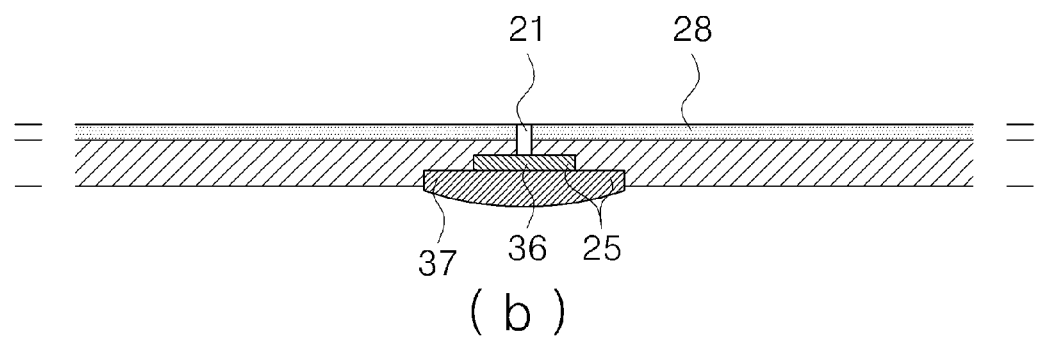

As illustrated in FIG. 10, the filling material injection groove 25 serves to prevent the filling material from leaking to the outside by closing the inlet 21 that has been opened after injecting the filling material into the silicone shell 10 and includes first and second sealing portions 36 and 37 formed of a sealant.

The first sealing portion 36 of the filling material injection groove 25 is formed by primarily sealing a space at a lower side of the inlet 21 so as to close the inner space of the silicone shell 10 from the outside. That is, the first sealing portion 36 prevents obstruction of the sealing process due to leakage of the filling material through the inlet 21 by the pressure applied to the silicone artificial breast prosthesis I in a process of sealing the filling material injection groove 25 after filling the inside of the silicone shell 10 with the filling material and prevents the sealing process from being unsatisfactorily performed due to operator error, such as incomplete wiping of the filling material off of the inlet 21 after filling with the filling material.

The sealant constituting the first sealing portion 36 may be a liquid silicone rubber (LSR) having a viscosity that enables sealing even though pressure is not applied to the filling material injection groove 25, i.e., a relatively low viscosity. In particular, the first sealing portion 36 may have a viscosity of 100 to 2,000 cps in consideration of safety and efficiency.

The second sealing portion 37 is formed by secondarily sealing a space at a lower side of the first sealing portion 36 to be finishing-processed so as to prevent the filling material injected into the inner space of the silicone shell from leaking to the outside. That is, the second sealing portion 37 is configured to more rigidly and doubly seal the filling material injection groove 25 that has been sealed by the first sealing portion 36 and may be smoothly molded and adhered by again applying pressure to the filling material injection groove 25 since the filling material is not leaked to the outside via the inlet 21 due to pressure applied to the silicone artificial breast prosthesis I by the first sealing portion 36.

The sealant constituting the second sealing portion 37 may be silicone in the form of silicone gum or LSR that can be molded and adhered through pressurization on the filling material injection groove 25, preferably, a sealant in the form of silicone gum.

In this regard, the silicone shell 10 and the patch adhesion portion P are formed of the above-described silicone polymer so as to have the same thickness and the same physical properties. In another embodiment, however, the thin film patch 28 and the patch 20 including an adhesive may be formed of a silicone material that has different physical properties from those of the silicone shell 10. This causes physical properties of the adhesion structure consisting of the thin film patch 28 and the patch 20 including an adhesive to be the same as those of the silicone shell 10 and is attributed to differences between the thicknesses of a barrier film included in the silicone shell 10 and the barrier film of the thin film patch 28 and differences in physical properties between the adhesion structures.

The adhesive for adhering the thin film patch 28 to the patch 20 or for adhering the patch 20 to the silicone shell 10 to form the patch adhesion portion P may be one selected from the above-described silicone raw materials, and examples thereof include a gum-type silicone adhesive and LSR adhesive.

When stress is applied to the adhesion boundary point at which the silicone shell 10 and the patch 20 are adhered to each other, the stress is dispersed in at least two axial directions such that stress applied in accordance with left and right tensile forces and stress applied according to tensile force in an inclination angle direction of a cross-section of the step portion 12 or uneven groove 13 and in an inclination angle direction of a cut cross-section of the patch hole are simultaneously applied to the patch adhesion portion P. More specifically, as stress applied to the adhesion structure between the elements of the patch adhesion portion P, i.e., stress at the adhesion boundary point therebetween, stress applied in a horizontal direction according to left and right tensile forces (horizontal direction stress), stress applied according to tensile force in a slope direction of a cross-section inclination angle of the patch hole 11 formed in the silicone shell 10 (slope direction stress), stress applied according to tensile force in an inclination angle direction of a cross-section of the step portion 12 or the uneven groove 13 formed at the patch hole 11 (slope direction stress), and stress applied according to tensile force in a vertical direction of a cross-section of the step portion 12 (vertical direction stress) are simultaneously applied to the patch adhesion portion P and dispersed in at least two axial directions. Thus, the patch adhesion structure exhibits the same effects as those of a structure consisting of the silicone shell 10 and has strong stress resistance.

Hereinafter, a method of manufacturing the above-described silicone artificial breast prosthesis with minimized stress concentration will be described.

Figure 11:
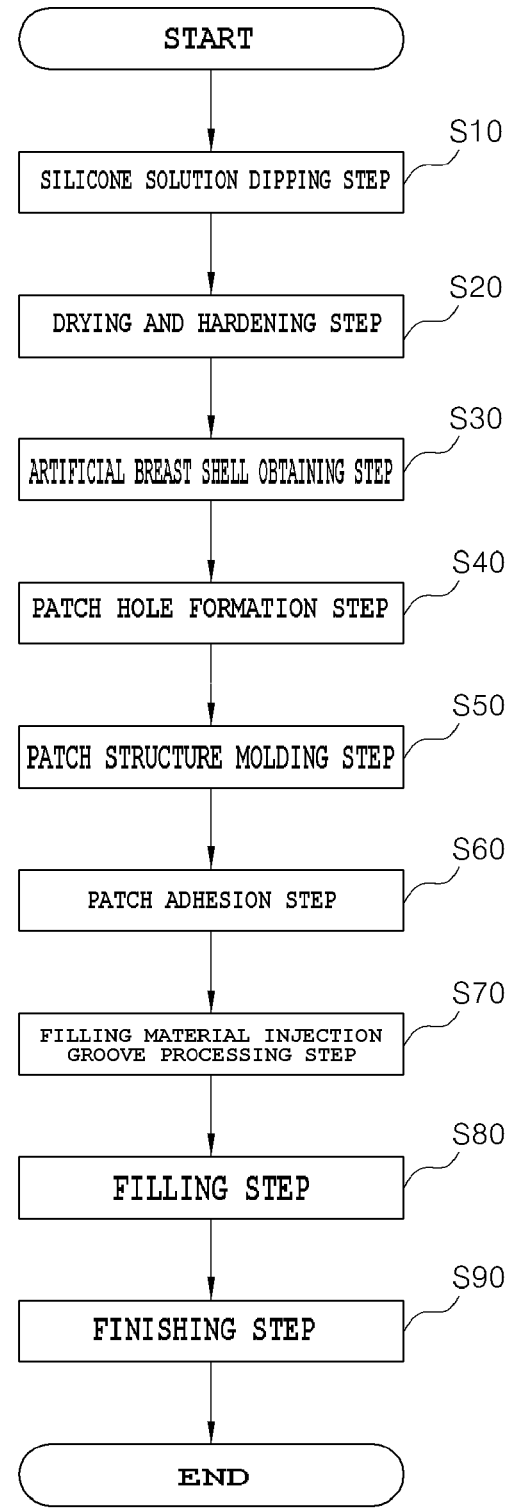
FIG. 11 is a flowchart illustrating an artificial breast prosthesis fabrication method according to an embodiment of the present invention.

First, as illustrated in FIG. 11, a method of manufacturing the silicone artificial breast prosthesis with minimized stress concentration, according to an embodiment of the present invention, includes a silicone solution dipping step S10, a drying and hardening step S20, an artificial breast shell obtaining step S30, a patch hole formation step S40, a patch structure molding step S50, a patch adhesion step S60, a filling material injection groove processing step S70, a filling step S80, and a finishing step S90.

In the silicone solution dipping step S10, a breast-shaped mold is dipped into a container containing a silicone solution to coat an overall surface of the mold with the silicone solution, to obtain an initial silicone shell 10 of the artificial breast prosthesis.

In the drying and hardening step S20, the mold dipped into the silicone solution is dried and hardened to obtain the silicone shell 10 constituting the artificial breast prosthesis I. That is, to obtain the silicone shell 10, the mold is placed inside a drying device and then the silicone shell 10 attached to the mold is dried and hardened.

In the artificial breast shell obtaining step S30, a hole is perforated in a lower end of the silicone shell 10 attached to the mold and the silicone shell 10 is detached from the mold and obtained.

In the patch hole formation step S40, the patch hole 11 to which the patch 20 is adhered is formed at an inner side of the hole formed in the lower end of the silicone shell 10. That is, the step portion 12 having a step is formed at the inner side of the hole in the lower end of the silicone shell 10 so as to allow the patch 20 to be adhered thereto, and the uneven grooves 13 are formed at the step portion 12.

To form the step portion 12 and the uneven grooves 13 at the silicone shell 10, first, the silicone shell 10 is turned inside out using the patch hole 11 formed at the silicone shell 10 so that an inner surface of the silicone shell 10 is turned outside, the silicone shell 10 is mounted on a separate jig to perform processing of the step portion 12 thereon, and the uneven grooves 13 are processed at the step portion 12.

In the patch hole formation step S40, the step portion 12 and the uneven grooves 13, to which the patch 20 may be adhered, may be formed at the lower surface of the silicone shell 10 through mechanical etching.

In addition, in the patch hole formation step S40, the step portion 12 and the uneven grooves 13, to which the patch 20 may be adhered, may be formed at the lower surface of the silicone shell 10 through chemical etching or laser processing.

In the patch structure molding step S50, a patch structure, i.e., the thin film patch 28 and the patch 20 including an adhesive, is molded to correspond to shapes of the step of the step portion 12 and the patch hole 11 including the uneven grooves 13 as well as circumference and thickness of the patch hole 11 so that the patch 20 including the thin film patch 28 is completely adhered to the patch hole 11 of the silicone shell 10 with no gap therebetween.

In the patch structure molding step S50, the patch structure is processed through press compression molding after placing the thin film patch 28 and the patch 20 including an adhesive in a molding frame having shape, circumference and thickness corresponding to those of the step portion 12 and the uneven grooves 13 of the patch hole 11.

In the patch adhesion step S60, the patch structure is adhered to the patch hole 11 of the silicone shell 10.

To adhere the patch structure obtained through the patch structure molding step S50 to the patch hole 11 of the silicone shell 10, the step portion 12 and the uneven grooves 13 of the patch hole 11 are turned so as to be placed at an inner side of the silicone shell 10, and the patch structure is accurately aligned with the patch hole 11 at the inner side of the silicone shell 10 and then adhered thereto through press compression processing and heating.

When forming the patch adhesion portion P at the patch hole 11 of the silicone shell 10, a silicone bonding device such as a pressing device, or the like is generally used. In this regard, configuration and operating principle of silicone bonding devices can be easily understood by those skilled in the art, and thus, a detailed description thereof will be omitted herein.

In this regard, the patch adhesion portion P formed through the patch adhesion step S60 has the same thickness as that of the silicone shell 10 and mechanically has the same physical properties as the silicone shell 10, and thus, stress concentration occurring due to differences in physical properties between the silicone shell 10 and the patch adhesion portion P is minimized, whereby overall fatigue resistance of the artificial breast prosthesis I is enhanced. In addition, the patch adhesion structure of the patch adhesion portion P is a structure in which neither a gap nor a crack is formed at an adhesion boundary point between the silicone shell 10 and the patch 20 and includes the step portion 12 and the uneven grooves 13 that increase an adhesion area between the silicone shell 10 and the patch 20. In addition, the patch adhesion structure has a structure in which the patch 20 including the thin film patch 28 is adhered to an inner surface of the silicone shell 10 and thus stress applied to the artificial breast prosthesis I is more satisfactorily dispersed and has mechanically and physically strong resistance to the pressure applied to the artificial breast prosthesis I and thus provides enhanced adhesion durability of the patch adhesion portion P.

Figure 2:
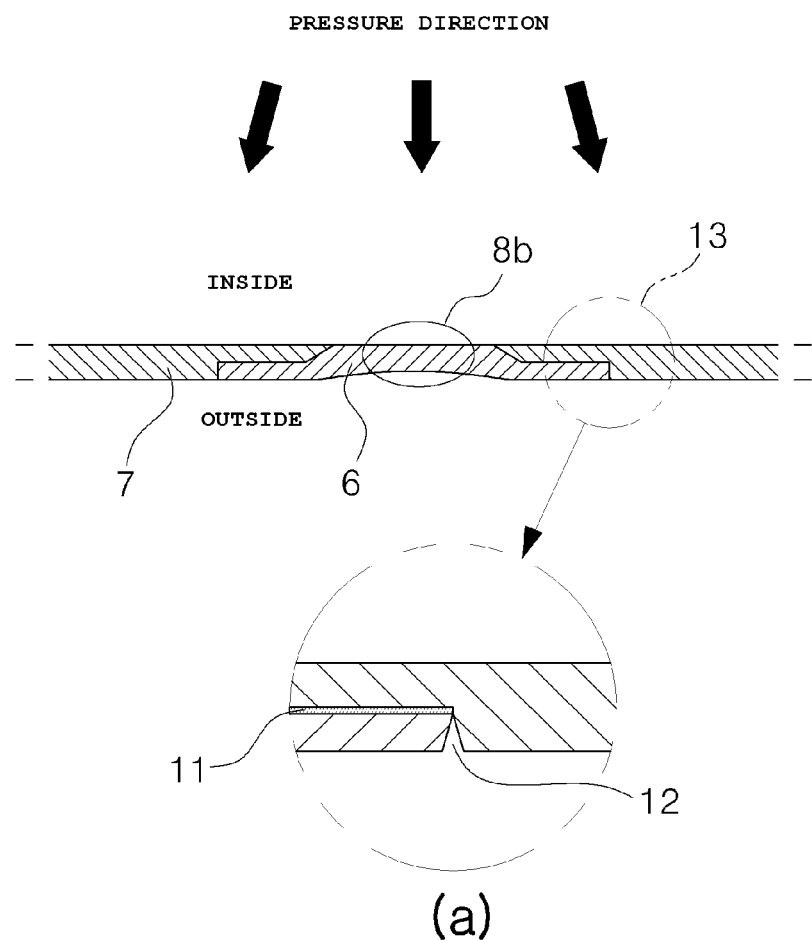
FIGS. 2(a) and 2(b) are views illustrating other examples of a silicone shell and a patch adhesion portion of a conventional artificial breast prosthesis.
Figure 2:
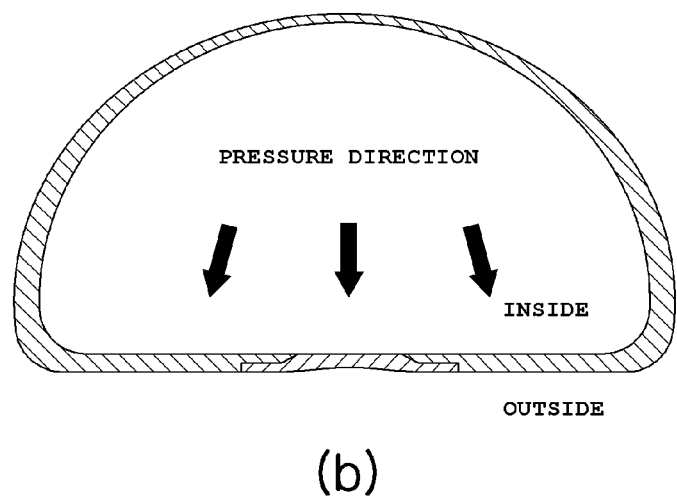
Figure 3:
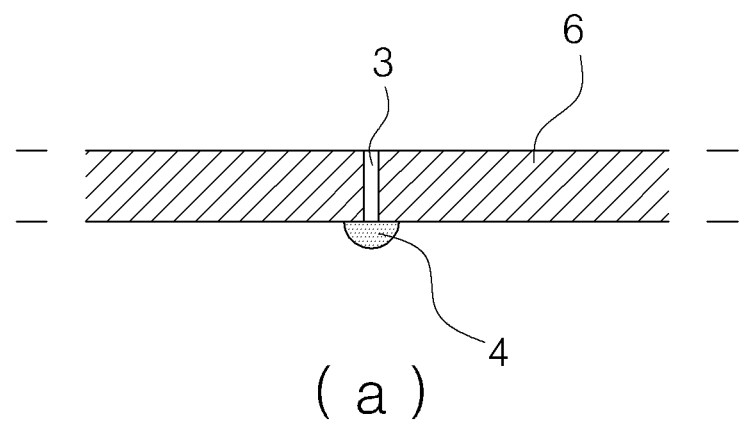
FIGS. 3(a) and 3(b) are views illustrating examples of finishing processes of a patch adhesion portion of a conventional artificial breast prosthesis.
Figure 3:
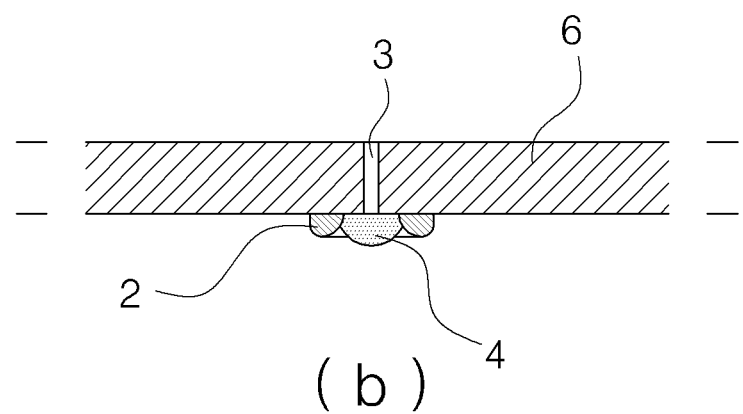
Figure 4:
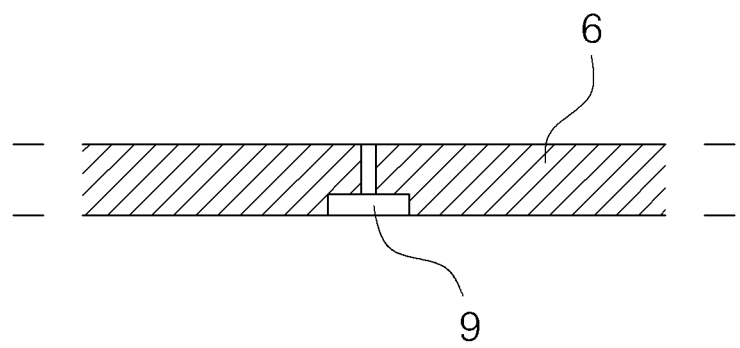
FIGS. 4(a) and 4(b) are views illustrating other examples of finishing processes of a patch adhesion portion of a conventional artificial breast prosthesis.
Figure 4:
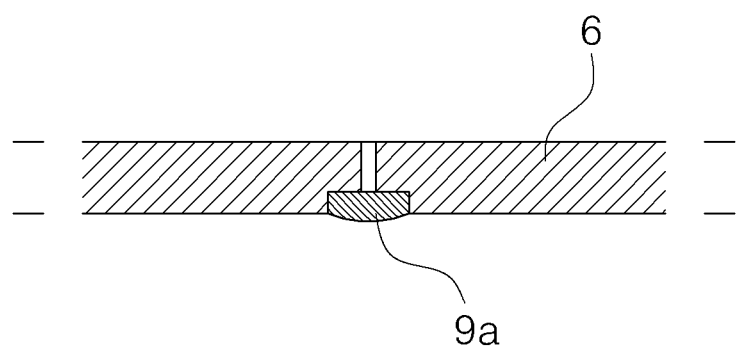

By contrast, in a conventional patch adhesion structure, as illustrated in FIGS. 1(a) and 1(b), the silicone shell 7 has an average thickness of 0.5 to 1 mm, while the patch adhesion portions 8a and 8b have a thickness of 1.3 to 3 mm and a central portion thereof has a thickness of 0.3 to 0.8 mm. Thus, differences in physical properties between the silicone shell 7 and the patch adhesion portions 8a and 8b are so significant that substantial stress is concentrated at a boundary therebetween and thus the conventional patch adhesion structure exhibits poor fatigue resistance. In addition, conventionally, as illustrated in FIG. 2(a), the silicone shell 7 has an average thickness of 0.5 to 1 mm while a central portion of the adhesion portion has a thickness of 0.3 to 0.8 mm, and thus, differences in physical properties between the silicone shell 7 and the patch adhesion portions 8a and 8b are so significant that substantial stress is concentrated at a boundary therebetween and, accordingly, the conventional patch adhesion structure exhibits poor fatigue resistance. In addition, as illustrated in FIGS. 2(a) and 2(b), a conventional patch adhesion structure has gaps or cracks 12 at the adhesion boundary point 13 between the silicone shell 7 and the patch adhesion portion 6 or has deteriorated adhesion durability due to weakness to pressure applied to an artificial breast prosthesis since a patch is adhered to an outer surface of the silicone shell 7.

However, the patch adhesion portion P according to the present invention has the same thickness and physical properties as the silicone shell 10 and thus exhibits very high stress resistance. Accordingly, while having a small thickness, the patch adhesion portion P rather has strong adhesion strength and exhibits high stress resistance and thus has high durability and enhances overall durability of the silicone artificial breast prosthesis I.

In the filling material injection groove processing step S70, the filling material injection groove 25 having a concave shape and a multilayered structure is formed at a lower surface of the patch 20, as a portion through which a filling material is injected into an inner space of the silicone shell 10 using a separate syringe device.

The filling material injection groove 25 may be formed through compression molding by pressing a central portion of the lower surface of the patch using a mold (not shown) having a molding part that has a convex shape corresponding to the shape of the filling material injection groove 25 and protrudes outwards.

In addition, in the filling material injection groove processing step S70, the filling material injection groove 25 may be formed through laser processing, mechanical etching, or chemical etching so as to have a concave shape.

As examples of formation of the filling material injection groove 25 through laser processing, the filling material injection groove 25 having a multilayered structure may be formed by emitting laser beams, as a high intensity heat source, to a lower surface of the patch 20, or the filling material injection groove 25 may be formed by performing laser sanding on a lower surface of the patch 20.

In the filling step S80, the inner space of the silicone shell 10 is filled with a filling material through injection via the inlet 21 from the patch provided thereat with the filling material injection groove 25.

The inlet 21 may be formed in a process of forming the filling material injection groove 25 in the filling material injection groove processing step S70, or the inlet 21 may be naturally formed in a process of injecting a filling material using a syringe device in the filling step S80.

In the finishing step S90, the filling material injection groove 25 is sealed by a sealant so that leakage of the filling material included in the silicone shell 10 to the outside via the inlet 21, which is a fine hole formed by a syringe needle when injecting the filling material, is prevented.

In sealing of the filling material injection groove 25 to close the inlet 21, the filling material injection groove 25 is completely and doubly sealed by primarily forming the first sealing portion 36 using a sealant having a low viscosity and secondarily forming the second sealing portion 37 thereon in the remaining space of the filling material injection groove 25.

Thus, the first and second sealing portions 36 and 37 formed through the finishing step S90 have an increased adhesion area due to the multilayered structure thereof. In addition, sealable silicone used in sealing treatment of the inlet 21 and edge portions thereof do not rub against the outside and thus the sealing portion of the inlet has high adhesion and high resistance to fatigue rupture and, accordingly, there is no risk of detachment of the sealable silicone from the sealing portion of the inlet 21, which results in increased protection against leakage of the filling material. In addition, since the inlet 21 is doubly sealed using the filling material injection groove 25 having a multilayered structure, deterioration of adhesive strength of the sealing portion of the inlet 21 due to leakage of the filling material via the inlet 21 occurring in the filling process may be prevented and problems occurring due to operator error may also be addressed, and thus, protection against leakage of the filling material may be increased.

That is, according to the silicone artificial breast prosthesis with minimized stress concentration according to the present invention and the manufacturing method thereof, a silicone shell has a uniform thickness and a patch adhesion portion has the same thickness as that of the silicone shell and the same or similar physical properties (expansibility, strength, elasticity, and the like) to the silicone shell, and thus, stress concentration occurring due to differences in physical properties between the silicone shell and the patch adhesion portion is minimized and resistance to fatigue rupture is maximized and, accordingly, rupture of the artificial breast prosthesis, which is the most dangerous complication, is significantly reduced, whereby safety and efficacy of the artificial breast prosthesis may be enhanced.

In addition, the patch adhesion portion includes a step portion and an uneven groove and has an adhesion structure having high mechanical and physical resistance to pressure applied to the artificial breast prosthesis in which a patch is adhered to an inner surface of the silicone shell. In this regard, the adhesion structure increases an adhesion area and allows stress to be dispersed in at least two axial directions, and thus, adhesive strength is mechanically and physically increased and adhesion durability of the patch adhesion portion is enhanced, which results in enhanced overall safety of the artificial breast prosthesis.

In addition, the patch adhesion portion has a structure in which neither a gap nor a crack is formed at an adhesion boundary point between the silicone shell and the patch and thus may have enhanced adhesion durability.

In addition, the silicone shell including the patch and the patch adhesion portion has a uniform overall thickness and thus the artificial breast prosthesis has excellent overall feel and, accordingly, may have high efficacy and quality.

In addition, a finishing process is performed through double sealing so that an inlet formed through injection of a filling material and a silicone sealant for closing the inlet or edge portions thereof are not exposed to the outside, and thus, beautiful appearance of the sealing portion of the inlet may be achieved.

Moreover, sealing portions of a filling material injection groove have an increased adhesion area due to a multilayered structure thereof and a sealable silicone used in sealing of the inlet and edge portions thereof do not rub against the outside, and thus, an inlet sealing portion has increased adhesive strength and enhanced resistance to fatigue rupture and, accordingly, there is no risk of detachment of the sealable silicone from the inlet sealing portion, which results in increased protection against leakage of the filling material.

Furthermore, the filling material injection groove has a multilayered structure and doubly seals the inlet, and thus, deterioration of adhesive strength of the sealing portion of the inlet due to leakage of the filling material via the inlet occurring in the filling process may be prevented and problems occurring due to operator error may also be addressed, and thus, protection against leakage of the filling material may be maximized.

Although the preferred embodiments of a silicone artificial breast prosthesis with minimized stress concentration and a method of manufacturing the same have been disclosed for illustrative purposes, those skilled in the art will appreciate that various modifications, additions and substitutions are possible, without departing from the scope and spirit of the invention as disclosed in the accompanying claims.

| Description of Reference Numerals | |
| --- | --- |
| 10: Silicone shell | 11: Patch hole |
| 12: Step portion | 13: Uneven groove |
| 15: Curved surface | 16: Slope |
| 20: Patch | 21: Inlet |
| 25: Filling material injection groove | |
| 28: Thin film patch | |
| 36: First sealing portion | 37: Second sealing portion |
| I: Prosthesis | P: Patch adhesion portion. |

What is claimed is:

1. A silicone artificial breast prosthesis with minimized stress concentration, the silicone artificial breast prosthesis comprising a silicone shell forming an outer wall thereof and a patch adhesion portion for closing a hole formed in a lower surface of the silicone shell from the outside, wherein the silicone shell has a uniform overall thickness, the patch adhesion portion has a patch hole to which a patch is adhered by an adhesive to an inner lower end of the silicone shell, and the patch adhesion portion in which the patch is adhered to the patch hole has the same thickness as that of the silicone shell and the same or similar physical properties as the silicone shell wherein the patch hole has at least one step portion having a step and formed at an inner surface of a portion of the silicone shell contacting the patch.

2. The silicone artificial breast prosthesis according to claim 1, wherein the patch hole has a slope such that the patch hole increases in diameter towards the step portion from a bottom of the patch hole to an upper side thereof.

3. The silicone artificial breast prosthesis according to claim 1, wherein the patch hole has a rounded concave curved surface formed along an outer circumference of the step portion.

4. A silicone artificial breast prosthesis with minimized stress concentration, the silicone artificial breast prosthesis comprising a silicone shell forming an outer wall thereof and a patch adhesion portion for closing a hole formed in a lower surface of the silicone shell from the outside, wherein the silicone shell has a uniform overall thickness, the patch adhesion portion has a patch hole to which a patch is adhered by an adhesive to an inner lower end of the silicone shell, and the patch adhesion portion in which the patch is adhered to the patch hole has the same thickness as that of the silicone shell and the same or similar physical properties as the silicone shell wherein the patch hole is configured such that a diameter of the patch hole on an inner side of the silicone shell is greater than that of the patch hole on an outer side of the silicone shell.

5. The silicone artificial breast prosthesis according to claim 1, wherein the patch adhesion portion has at least one uneven groove at a surface of the patch adhesion portion contacting the patch and adhesion durability therebetween is enhanced so as to prevent the patch from detaching from the patch adhesion portion.

6. The silicone artificial breast prosthesis according to claim 5, wherein the uneven groove has a V-letter shape or a U-letter shape.

7. The silicone artificial breast prosthesis according to claim 1, wherein the patch comprises a leakage prevention layer of low molecular weight silicone.

8. The silicone artificial breast prosthesis according to claim 1, wherein the patch adhesion portion comprises a bonding material or an adhesive disposed between the silicone shell and the patch so as to enable smooth adhesion therebetween.

9. The silicone artificial breast prosthesis according to claim 1, wherein the patch adhesion portion is completely adhered such that an inner surface of the silicone shell and an inner surface of the patch form the same horizontal plane to prevent occurrence of a gap or a crack at an adhesion boundary point between the silicone shell and the patch.

10. A silicone artificial breast prosthesis with minimized stress concentration, the silicone artificial breast prosthesis comprising a silicone shell forming an outer wall thereof and a patch adhesion portion for closing a hole formed in a lower surface of the silicone shell from the outside, wherein the silicone shell has a uniform overall thickness, the patch adhesion portion has a patch hole to which a patch is adhered by an adhesive to an inner lower end of the silicone shell, and the patch adhesion portion in which the patch is adhered to the patch hole has the same thickness as that of the silicone shell and the same or similar physical properties as the silicone shell wherein the patch adhesion portion comprises at least one thin film patch formed thin.

11. The silicone artificial breast prosthesis according to claim 1, wherein the patch adhesion portion comprises an inlet formed above a lower surface thereof so that a filling material is injected into an inner space of the silicone shell and a filling material injection groove disposed below the inlet, having a multilayered structure comprising at least two layers, and concavely formed.

12. The silicone artificial breast prosthesis according to claim 11, wherein the filling material injection groove comprises a first sealing portion formed by primarily sealing a space at a lower side of the inlet so as to close the inner space of the silicone shell from the outside and a second sealing portion formed by secondarily sealing a space at a lower side of the first sealing portion to be finishing-processed so as to prevent the filling material injected into the inner space of the silicone shell from leaking to the outside.

13. The silicone artificial breast prosthesis according to claim 1, wherein the adhesive is a silicone adhesive in the form of gum or a liquid silicone rubber (LSR) adhesive.

14. The silicone artificial breast prosthesis according to claim 1, wherein, when stress is applied to the adhesion boundary point at which the silicone shell and the patch are adhered to each other, the stress is dispersed in at least two axial directions such that stress applied in accordance with left and right tensile forces and stress applied according to tensile force in an inclination angle direction of a cross-section of the step portion or uneven groove and in an inclination angle direction of a cut cross-section of the patch hole are simultaneously applied to the patch adhesion portion.

15. The silicone artificial breast prosthesis according to claim 10, wherein the patch hole has a slope such that the patch hole increases in diameter towards the step portion from a bottom of the patch hole to an upper side thereof.

16. The silicone artificial breast prosthesis according to claim 10, wherein the patch hole has a rounded concave curved surface formed along an outer circumference of the step portion.

17. The silicone artificial breast prosthesis according to claim 10, wherein the patch adhesion portion has at least one uneven groove at a surface of the patch adhesion portion contacting the patch and adhesion durability therebetween is enhanced so as to prevent the patch from detaching from the patch adhesion portion.

18. The silicone artificial breast prosthesis according to claim 17, wherein the uneven groove has a V-letter shape or a U-letter shape.

19. The silicone artificial breast prosthesis according to claim 10, wherein the patch comprises a leakage prevention layer of low molecular weight silicone.

20. The silicone artificial breast prosthesis according to claim 10, wherein the patch adhesion portion comprises a bonding material or an adhesive disposed between the silicone shell and the patch so as to enable smooth adhesion therebetween.

21. The silicone artificial breast prosthesis according to claim 10, wherein the patch adhesion portion is completely adhered such that an inner surface of the silicone shell and an inner surface of the patch form the same horizontal plane to prevent occurrence of a gap or a crack at an adhesion boundary point between the silicone shell and the patch.

22. The silicone artificial breast prosthesis according to claim 10, wherein the patch adhesion portion comprises an inlet formed above a lower surface thereof so that a filling material is injected into an inner space of the silicone shell and a filling material injection groove disposed below the inlet, having a multilayered structure comprising at least two layers, and concavely formed.

23. The silicone artificial breast prosthesis according to claim 22, wherein the filling material injection groove comprises a first sealing portion formed by primarily sealing a space at a lower side of the inlet so as to close the inner space of the silicone shell from the outside and a second sealing portion formed by secondarily sealing a space at a lower side of the first sealing portion to be finishing-processed so as to prevent the filling material injected into the inner space of the silicone shell from leaking to the outside.

24. The silicone artificial breast prosthesis according to claim 10, wherein the adhesive is a silicone adhesive in the form of gum or a liquid silicone rubber (LSR) adhesive.

25. The silicone artificial breast prosthesis according to claim 10, wherein, when stress is applied to the adhesion boundary point at which the silicone shell and the patch are adhered to each other, the stress is dispersed in at least two axial directions such that stress applied in accordance with left and right tensile forces and stress applied according to tensile force in an inclination angle direction of a cross-section of the step portion or uneven groove and in an inclination angle direction of a cut cross-section of the patch hole are simultaneously applied to the patch adhesion portion.

\* \* \* \* \*